United States Patent [19]
Steinmann et al.

[11] Patent Number: 5,658,712
[45] Date of Patent: Aug. 19, 1997

[54] (METH)ACRYLATES CONTAINING URETHANE GROUPS

[75] Inventors: Bettina Steinmann, Praroman; Jean-Pierre Wolf, Courtaman; Adrian Schulthess, Tentlingen; Max Hunziker, Düdingen, all of Switzerland

[73] Assignee: Ciba-Geigy Corporation, Tarrytown, N.Y.

[21] Appl. No.: 552,643

[22] Filed: Nov. 3, 1995

Related U.S. Application Data

[62] Division of Ser. No. 286,061, Aug. 4, 1994, Pat. No. 5,495,029.

[30] Foreign Application Priority Data

Aug. 9, 1993 [CH] Switzerland .............. 2370/93

[51] Int. Cl.$^6$ .............................................. C07C 271/00
[52] U.S. Cl. ................................... 430/325; 526/301
[58] Field of Search ........................... 430/325; 526/301

[56] References Cited

U.S. PATENT DOCUMENTS

| | | | |
|---|---|---|---|
| 4,100,141 | 7/1978 | O'Sullivan | 526/301 |
| 4,465,718 | 8/1984 | Gruber | 528/49 |
| 4,575,330 | 3/1986 | Hill | 425/174.4 |
| 4,879,402 | 11/1989 | Reiners et al. | 560/26 |
| 4,952,241 | 8/1990 | Reiners et al. | 106/35 |
| 5,059,511 | 10/1991 | Higashi et al. | 430/272 |

FOREIGN PATENT DOCUMENTS

| | | |
|---|---|---|
| 0111259 | 6/1984 | European Pat. Off. |
| 0264551 | 4/1988 | European Pat. Off. |
| 0360869 | 4/1990 | European Pat. Off. |

OTHER PUBLICATIONS

Derwent Abst. 90–269062/36 (1990).
Polym. Mat. Sci. Eng. 61, (1989), pp. 302–311.
Derwent Abst. 87–182231/26 (1987).
C.A. vol. 107, 1987, 2005070a.
Derwent Abst. 87–182232/26 (1987).
C.A. vol. 107, 1987, 219251u.
Rev. Sci. Instrum. 52(11), Nov. 1981, pp. 1770–1773.
Chemical Abst. 84:165551c (1976).
Chemical Abst. 96: 218764f (1982).

*Primary Examiner*—Richard L. Raymond
*Attorney, Agent, or Firm*—David R. Crichton

[57] ABSTRACT

Novel (meth)acrylates which also contain urethane groups and other polymerizable groups in one and the same molecule and can be polymerized either by means of free radicals and/or cationically are used for the production of coatings, adhesives, photoresists, solder masks or in stereolithography. The mouldings produced therefrom contain a coherent, homogeneous network and have high strength properties, in particular mechanical properties.

14 Claims, No Drawings

(METH)ACRYLATES CONTAINING URETHANE GROUPS

This is a divisional of Ser. No. 08/286,061, filed Aug. 4, 1994, now U.S. Pat. No. 5,495,029.

The present invention relates to novel (meth)acrylates containing urethane groups, to the preparation thereof, and to a process for the polymerization of these compounds by means of actinic irradiation, and to their use, for example in stereolithography for the production of three-dimensional articles, and to the use of the novel (meth)acrylates containing urethane groups, in particular for the production of coating compositions, adhesives, photoresists and solder masks.

As is known, radiation-sensitive resins or resin mixtures can be used in a variety of ways, for example as coating compositions, adhesives or photoresists. In principle, these resins or resin systems should in general also be suitable for the production of three-dimensional (3D) objects by the stereolithographic process described in U.S. Pat. No. 4 575 330, but many resins prove to be excessively viscous, and others are insufficiently photosensitive or undergo excessive shrinkage on curing. Moreover, the strength properties of the mouldings or objects made from photocured resins are frequently unsatisfactory.

As is known, stereolithography can be used to produce complex three-dimensional objects from liquid, photosensitive resins. Such objects are built up in layers, each new curable resin layer being strongly bonded to the preceding, pre-cured layer by pre-curing by means of UV/VIS light. As is known, the three-dimensional object as a whole can be built up by a computer-controlled process.

There has been no lack of attempts in recent years to develop resin systems which can be employed in stereolithographic processes. H. Kodama, in Rev. Sci. Instrum. 52 (11), 1770–1773, (1981), discloses, under the trade name "Tevista", a liquid, photocurable resin mixture comprising an unsaturated polyester, an acrylic ester, styrene, a polymerization initiator and a sensitizer. However, this resin system has the disadvantage for stereolithography that the photosensitivity is inadequate and the green strength of the objects pre-cured by laser beams is relatively low.

U.S. Pat. No. 4,575,330 proposes a stereolithographic process in which the liquid resin employed is a modified acrylate referred to in the description as "Potting Compound 363". Such resin mixtures are disclosed in U.S. Pat. No. 4,100,141. They too have the disadvantage of inadequate photosensitivity, and long times are required for the production of three-dimensional objects by stereolithography.

It is therefore understandable that very high demands are made of resins to be employed in stereolithography. For example, the photosensitivity of the resin system should be such that the ratio between the radiation energy used and the penetration depth achieved into the liquid photosensitive resin mixture, where the parts in question solidify, is within acceptable limits. This means, for a resin or resin mixture which is suitable for stereolithography, that the aim is to achieve the greatest possible curing depth at the same time as a high degree of polymerization and good green strength using little radiation energy.

In the process of consecutive polymerization of thin layers, as used in stereolithography, none of these layers is usually cured completely. The incompletely cured object is referred to as a green product, and the modulus of elasticity and the fracture strength of this green product are also known as the green strength. The green product is normally then cured with UV and/or VIS light, for example by means of a mercury or xenon arc lamp. The green strength of a workpiece is therefore an important parameter, since objects of low green strength can deform under their own weight or can sag or collapse on curing.

In the prior art, EP-A-0 360 869, inter alia, proposes mixtures of acrylate compounds with epoxy resins as usable compounds, in particular for stereolithography. However, these mixtures have the disadvantage of giving brittle end products. In addition, curing gives two independent networks, which has an adverse effect on the green strength and the final properties.

Furthermore, JP-A 046 956, JP-A-2 479 39 and JP-A 2 479 38 disclose acrylate structures containing urethane groups and further polymerizable groups which can be employed in stereolithography. However, these acrylates can only be polymerized by means of free radicals, since the further polymerizable groups are acrylates or allyl compounds.

The object of the invention was therefore to develop compounds which overcome the above disadvantages, i.e. have the correct viscosity and photosensitivity for stereolithographic applications, and which do not have an independent network, but instead a coherent, homogeneous network, so that the strength properties of the mouldings and the mechanical properties in general can be improved.

This object has been achieved by a new class of polymerizable (meth)acrylates containing urethane groups. These contain both at least one (meth)acrylate group and at least one urethane group and also a further polymerizable group in one and the same molecule and accordingly are multifunctional compounds.

These compounds can be obtained by reacting OH-containing (meth)acrylates with a diisocyanate and subsequently with an alcohol containing the desired polymerizable groups (or from which the polymerizable group can be prepared). The above JP-A publications only disclose products of the reaction of OH-containing acrylates with a diisocyanate and an acrylate- or allyl-containing alcohol. This gives either tetrafunctional acrylates (in which all the acrylate groups react by the same mechanism and at the same rate) or difunctional acrylates containing two allyl groups. However, these allyl groups can only be polymerized thermally, but not by means of free-radicals using a photoinitiator.

By contrast, one class of the novel (meth)acrylates containing urethane groups also contains, in addition to the (meth)acrylate groups, cationically polymerizable groups which react by a different mechanism and at a different rate. Another class contains, in addition to the (meth)acrylate groups, further free-radical-polymerizable groups, which can undergo a polyaddition either by means of free radicals with a photoinitiator (but at a different rate from acrylates) or with addition of thiols and a photoinitiator in so-called thiol-ene systems.

It is surprising that, firstly, such molecules can be prepared relatively easily and can readily be polymerized by means of free radicals and/or cationically and, secondly, that these compounds are suitable for use, for example, in stereolithography.

Irradiation of the compositions prepared from these novel polymerizable (meth)acrylates containing urethane groups thus allows various crosslinking densities to be achieved, with the consequence that both the green products formed on pre-curing by means of laser beams and the objects obtained by curing the green products are distinguished by mostly good mechanical properties, in particular strength properties, which can be varied within broad limits.

The present invention thus relates to novel (meth) acrylates which also contain urethane groups and at least one other polymerizable group in the molecule and thus represent a hybrid system containing two different functional groups which can be polymerized by different mechanisms. They can be either open-chain structures or structures containing ring elements.

Of particular interest are polymerizable (meth)acrylates of the formula (I) containing urethane groups

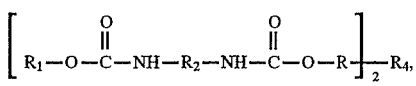

in which
R is a divalent group of the formula

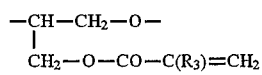

or

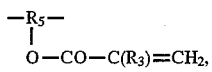

$R_1$ is a cationically polymerizable group or a free-radical-polymerizable group, but not an acrylate or allyl group,
$R_2$ is an aliphatic, cycloaliphatic or aromatic radical,
$R_3$ is hydrogen or $CH_3$,
$R_4$ is the radical of an aliphatic, cycloaliphatic or aromatic diglycidyl compound after removal of the diglycidyl radical, or is the radical of a cycloaliphatic diepoxide, and $R_5$ is a cycloaliphatic bridge.
If R is a group of the formula

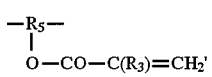

the —O—CO—C($R_3$)=$CH_2$ radical of this group is on the $R_5$ radical, preferably in the o-position to the —O—CO—NH— bond.

If $R_1$ is a cationically polymerizable group, all known cationically polymerizable groups are in principle suitable, in particular those which conform to the following formulae:

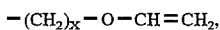

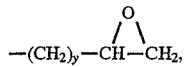

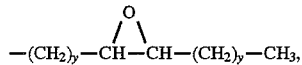

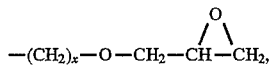

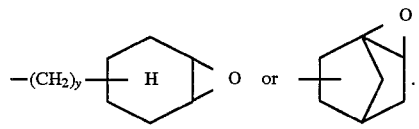

The —(CH$_2$)$_x$— group in these formulae can be interrupted once or more than once, in particular by arylene, such as phenylene or naphthylene, or alternatively by $C_5$- or $C_6$cycloalkylene groups, such as, in particular, cyclohexylene.

Particularly preferred cationically polymerizable groups for $R_1$ conform to the formulae

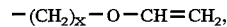

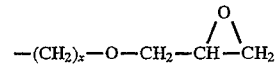

and

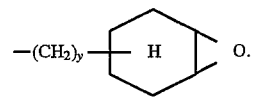

If $R_1$ is a free-radical-polymerizable group, all known groups, with the exception of the acrylate and allyl groups, are likewise suitable. Preference is given to those which conform to the formulae:

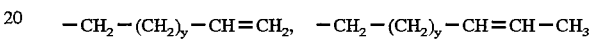

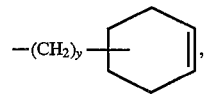

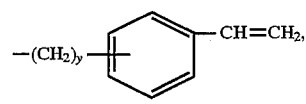

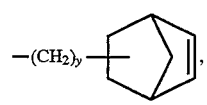

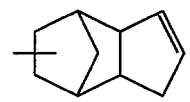

and

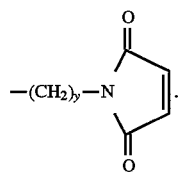

Particularly preferred free-radical-polymerizable groups conform to the formulae

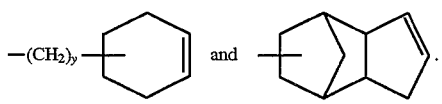

In all these formulae, x is an integer from 2 to 20, preferably from 2 to 6, and y is an integer from 1 to 20, preferably from 1 to 6.

In the preferred (meth)acrylates containing urethane groups, $R_1$ is a cationically polymerizable group.

If $R_2$ is an aliphatic, cycloaliphatic or aromatic radical and $R_4$ is the radical of an aliphatic, cycloaliphatic or aromatic diglycidyl compound or of a cycloaliphatic diepoxide, $R_2$ is, in particular, a $C_4$-$C_{20}$aliphatic bridge, which may be interrupted by at least one ether, ester, urethane, amide or arylene group, or is a cycloaliphatic or aromatic bridge.

$C_4$–$C_{20}$ aliphatic bridges are either straight-chain or branched aliphatic radicals, such as butylene radicals, or pentylene, hexylene, heptylene, octylene, nonylene, decylene, undecylene, dodecylene, tetradecylene, hexadecylene, icosylene or docosylene radicals.

Cycloaliphatic bridges $R_2$ and/or $R_4$ are in particular cyclohexylene and cyclopentylene radicals.

Aromatic bridges $R_2$ and/or $R_4$ are in particular arylene, such as phenylene or naphthylene, or a plurality of arylene groups, which may be interrupted by aliphatic radicals, for example diphenylmethane or bisphenol A or F radicals after removal of the oxygen atoms.

Both the cycloaliphatic bridges and the aromatic bridges can be monosubstituted or polysubstituted, for example by $C_1$–$C_4$ alkyl (for example methyl, ethyl, n- or isopropyl, or n-, sec- or tert-butyl), $C_1$–$C_4$ alkoxy (for example methoxy or ethoxy) or halogen (fluorine, chlorine, bromine or iodine). $R_2$ is, for example, a bridge of the following formulae:

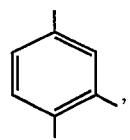

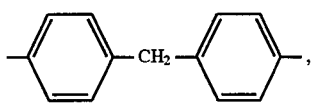

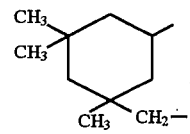

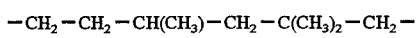

and

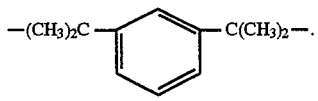

$R_4$ can be, for example, a bridge of the following formulae:

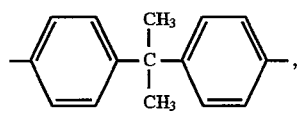

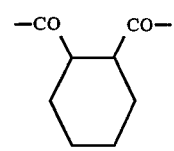

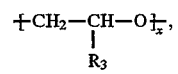

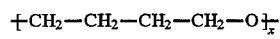

and

where x and y are as defined above.

In preferred (meth)acrylates containing urethane groups, $R_2$ is a $C_4$–$C_{20}$ aliphatic or an aromatic bridge or a plurality of aromatic groups interrupted by aliphatic groups, and $R_4$ is a $C_4$–$C_{20}$ aliphatic bridge interrupted by at least one ether or ester group, or is an aromatic bridge.

If $R_2$ and/or $R_4$ are an aliphatic bridge interrupted by ether or ester groups, the following radicals, for example, are suitable:

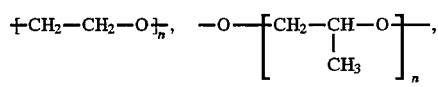

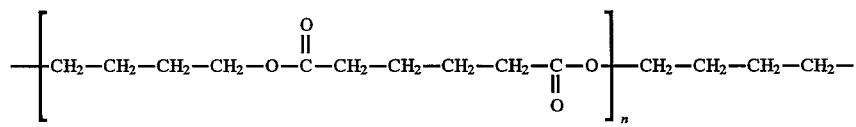

and

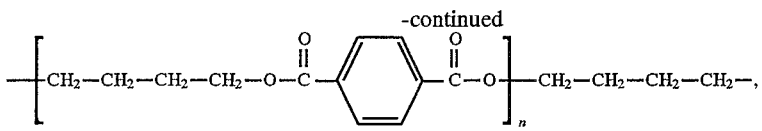

where n is an integer from 1 to 20.

Examples of cycloaliphatic bridges $R_5$ are cyclopentyl and cyclohexyl.

The novel (meth)acrylates containing urethane groups are low- to high-viscosity resins which are readily soluble in organic solvents, such as toluene, ethyl acetate and tetrahydrofuran.

The novel (meth)acrylates containing urethane groups can be employed in pure acrylate formulations. They increase the network density and thus the modulus of elasticity. In addition, they slow the reaction, giving SL mouldings of reduced (about 10–20%) curl.

It is surprising that the second polymerizable group can be introduced without problems into the existing diacrylate. Thus, the (meth)acrylate groups are not destroyed when the epoxide groups are introduced, and the very reactive vinyl ethers do not undergo any side reactions with the (meth) acrylates. It has been possible, surprisingly, to employ the novel urethane acrylates containing epoxy groups in hybrid systems, although the literature discloses that epoxides cannot be cationically polymerized in the presence of urethane groups (S. C. Lapin, Polym. Mater. Sci. Eng. 61, 302 (1989)).

The polymerizable (meth)acrylates containing urethane groups can be prepared in a manner known per se, for example by reacting an epoxyacrylate of the formula II

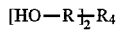  (II)

with a diisocyanate of the formula III

OCN—$R_2$—NCO   (III), expediently in equimolar amounts in an organic solvent, in the presence of a catalyst and in the presence of an inhibitor, and reacting the resultant compound of the formula IV

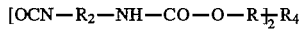   (IV)

with a compound which introduces the radical $R_1$. If desired, the resultant polymerizable (meth)acrylates of the formula I containing urethane groups can then be oxidized. $R_1$, $R_2$ and $R_4$ are as defined above.

Suitable epoxyacrylates of the formula II are all known types, for example bisphenol A diglycidyl diacrylate, butanediol diglycidyl diacrylate, bisphenol F diglycidyl diacrylate and polypropylene glycol diglycidyl diacrylate, and furthermore products of the reaction of acrylic acid with cycloaliphatic epoxy resins.

The diisocyanates of the formula III are likewise known and can be prepared in a known manner. Mention may be made, for example, of aliphatic, cycloaliphatic and aromatic diisocyanates, such as hexamethylene diisocyanate, trimethylhexamethylene diisocyanate, cyclohexane diisocyanate, isophorone diisocyanate (3,5,5-trimethyl-1-isocyanato-3-isocyanatomethylcyclohexane), methylenedicyclohexyl diisocyanate, p-phenylene diisocyanate, 2,4-diisocyanatotoluene, 2,6-diisocyantatotoluene and technical-grade mixtures of the two isomers, naphthylene diisocyanates, in particular 1,5-naphthylene diisocyanate, dianisidine diisocyanate, methylenediphenyl diisocyanates, in particular the 4,4'-isomer, but also technical-grade mixtures of various isomers, for example the 4,4'- and 2,4'-isomers, or polymethylenepolyphenylene diisocyanates; tolylene diisocyanate is particularly preferred.

The reaction of the epoxyacrylate of the formula II with the diisocyanate of the formula III is expediently carried out in an organic solvent in the presence of a catalyst and in the presence of an inhibitor at a temperature of about 30°–40° C., preferably at 35° C.

Examples of suitable organic solvents are: aromatic solvents, such as toluene and xylenes, and aliphatic solvents, such as chloroform, methylene chloride and ethyl acetate.

Examples of catalysts which can be employed are: dibutyltin dilaurate and tin octanoate.

Examples of inhibitors are 2,2'-methylenebis(6-tert-butyl-4-methylphenol) (=Ralox® 46), p-methoxyphenol and di-tert-butyl-p-cresol.

The reaction products of the formula IV obtained are known. They are reacted without isolation, i.e. in a one-step process, with a compound which introduces the radical $R_1$ to give the (meth)acrylates of the formula I containing urethane groups.

Suitable compounds which introduce the radical $R_1$ are those which contain at least one hydroxyl group. Examples of suitable compounds are alcohols, such as tetrahydrobenzyl alcohol and crotyl alcohol, and the corresponding alcohols of the radicals listed above as $R_1$.

The reaction of the compound of the formula IV with the compound which introduces the radical $R_1$ is advantageously carried out in the same solvent and at the same temperature as for the reaction of the epoxyacrylate of the formula II with the diisocyanate of the formula III. The organic solvent is subsequently removed by distillation, leaving a yellowish-white to yellow resin which corresponds to the polymerizable (meth)acrylate of the formula I containing urethane groups.

This resin can then be oxidized further. The oxidation is carried out, for example, using a solution of peracetic acid in acetic acid in the presence of an organic solvent, such as chloroform, methylene chloride or ethyl acetate, at a temperature of from 15° C. to a maximum of 40° C.

The novel (meth)acrylates containing urethane groups can be processed further with a very wide variety of components for the preparation of compositions. Such compositions comprise a) from 5 to 99% by weight of a monomeric, polymerizable (meth)acrylate of the formula I containing urethane groups, and b) from 1 to 10% by weight of a free-radical photoinitiator.

Typical compounds of known photoinitiators are benzoins, such as benzoin, benzoin ethers, such as benzoin methyl ether, benzoin ethyl ether, benzoin isopropyl ether and benzoin phenyl ether, benzoin acetate, acetophenones, such as acetophenone, 2,2-dimethoxyacetophenone and 1,1-dichloroacetophenone, benzil, benzil ketals, such as benzil dimethyl ketal and benzil diethyl ketal, anthraquinones, such as 2-methylanthraquinone, 2-ethylanthraquinone, 2-tert-butylanthraquinone, 1-chloroanthraquinone and 2-amylanthraquinone, furthermore triphenylphosphine, benzoylphosphine oxides, for example 2,4,6-trimethylbenzoyldiphenylphosphine oxide (Luzirin TPO), benzophenones, such as benzophenone and 4,4'-bis(N,N'-dimethylamino)benzophenone, thioxanthones and xanthones, acridine derivatives, phenazine derivatives, quinoxaline derivatives, 1-phenyl-1,2-propanedione 2-O-benzoyl oxime, 1-aminophenyl ketones and 1-hydroxyphenyl ketones, such as 1-hydroxycyclohexyl phenyl ketone, phenyl 1-hydroxyisopropyl ketone and 4-isopropylphenyl 1-hydroxyisopropyl ketone, all of which are known compounds.

Particularly suitable photoinitiators, which are usually used in combination with an He/Cd laser as light source, are acetophenones, such as 2,2-dialkoxybenzophenone, and 1-hydroxyphenyl ketones, for example 1-hydroxycyclohexyl phenyl ketone or 2-hydroxyisopropyl phenyl ketone (=2-hydroxy-2,2-dimethylacetophenone).

Another class of photoinitiators usually employed when argon ion lasers are used are benzil ketals, for example benzil dimethyl ketal.

A further class of suitable photoinitiators comprises ionic dye-counterion compounds, which are capable of absorbing actinic rays and generating free radicals which can initiate the polymerization of the epoxide compounds. The compositions containing ionic dye-counterion compounds can in this way be cured more variably by means of visible light in the accessible wavelength range from 400 to 700 nm. Ionic dye-counterion compounds and their mode of action are known, for example from EP Patent Application No. 223 587 and U.S. Pat. Nos. 4,751,102, 4,772,530 and 4,772,541. Examples which may be mentioned of suitable ionic dye-counterion compounds are: anionic dye-iodonium ion complexes, anionic dye-pyryllium ion complexes and in particular cationic dye-borate anion compounds of the formula

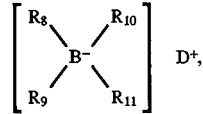

in which $D^+$ is a cationic dye, and $R_8$, $R_9$, $R_{10}$ and $R_{11}$, independently of one another, are each an alkyl, aryl, alkaryl, allyl, aralkyl, alkenyl, alkynyl, an alicyclic or saturated or unsaturated heterocyclic group. Preferred definitions for the radicals $R_8$ to $R_{11}$ are given, for example, in the above EP Patent Application 223 587.

As is known, the photoinitiators are added in effective amounts, i.e. expediently in amounts of from 2 to 10 per cent by weight, based on the total amount of the composition. If the novel compositions are to be used for stereolithographic processes, in which laser beams are normally employed, it is essential that the absorptivity of the composition is adjusted through the type and concentration of the photoinitiator in such a way that the curing depth for normal laser velocity is from approximately 0.1 to 2.5 mm.

Further suitable photoinitiators can also be compounds which have different radiation sensitivities to rays of emission lines of various wavelengths. These allow, for example, better utilization of a UV and/or VIS light source emitting emission lines of various wavelengths. It is advantageous here for the various photoinitiators to be selected in such a way and employed in such concentration that the same optical absorption is generated for the emission lines used.

Preferred photoinitiators are 1-hydroxyphenyl ketones, in particular 1-hydroxycyclohexyl phenyl ketone.

These compositions furthermore comprise:

c) from 0 to 20% by weight of conventional additives, for example stabilizers, such as UV stabilizers, polymerization inhibitors, release agents, wetting agents, flow-control agents, sensitizers, antisettling agents, surfactants, dyes, pigments or fillers;

d) from 0 to 80% by weight of one or more mono-, di- or polyfunctional (meth)acrylates, such as mono(meth)acrylates, mono-N-vinyl compounds having a maximum molecular weight of 500, aliphatic or cycloaliphatic di(meth)acrylates, aliphatic tri(meth)acrylates or aromatic di- or tri(meth)acrylates, or mixtures thereof;

e) from 0 to 80% by weight of one or more conventional di- or polyfunctional, aromatic, alicyclic or aliphatic epoxy resins, or mixtures thereof; epoxy resins which are suitable in the novel formulation are described, for example, in EP-A-0 360 869. Preference is given to butanediol diglycidyl ether and 3,4-epoxycyclohexyl 3',4'-epoxycyclohexanecarboxylate;

f) from 0 to 50% by weight of an OH-terminated polyether or polyester, such as di- or trifunctional polyether- or polyester-polyols, polytetrahydrofuran, poly-ε-caprolactone and OH-terminated polyurethanes or mixtures thereof. OH-terminated polycaprolactone is of particular interest;

g) from 0 to 5% by weight of a cationic photoinitiator, as described in EP-A-0 360 869; Triaryl hexafluoroantimonates, such as triarylsulfonium hexafluoroantimonates, are of particular interest;

h) 0–80% by weight of one or more mono-, di- or polyfunctional vinyl ethers, as described in EP 360 869.

Preferred compositions comprise a) from 10 to 60% by weight of a monomeric, polymerizable (meth)acrylate of the formula I containing urethane groups, b) from 0.5 to 7% by weight of a free-radical photoinitiator, c) from 0 to 10% by weight of conventional additives, d) from 10 to 70% by weight of one or more mono-, di- or polyfunctional (meth)acrylates, e) from 0 to 60% by weight of one or more di- or polyfunctional epoxides, f) from 0 to 50% by weight of an OH-terminated polyether or polyester, or mixtures thereof, g) from 0.5 to 5% by weight of a cationic photoinitiator, and h) from 0 to 60% by weight of one or more di- or polyfunctional vinyl ethers.

The compositions according to the invention, which have high photosensitivity, can be prepared in a known manner, for example by premixing individual components and subsequently mixing these premixes or by mixing all the components by means of conventional devices, such as stirred vessels, expediently in the absence of light and if necessary at slightly elevated temperature, for example from about 50° to 70° C.

The novel compositions containing coherent networks are liquids having a viscosity at 30° C. of from about 100 to 5000 mPas, preferably from 200 to 4500 mPas and in particular from 200 to 2000 mPas. These compositions surprisingly have high photosensitivity and a low curl factor both in hybrid systems and in acrylate systems, have high curing depth and good green strength, and the mouldings produced therefrom have excellent mechanical strength properties.

The compositions suitable according to the invention and containing the novel polymerizable (meth)acrylates containing urethane groups can be polymerized by irradiation with actinic light, for example by means of electron beams or X-rays, and furthermore by UV or VIS light, i.e. by means of electromagnetic radiation or particle beams in the wavelength range from 280 to 650 nm. Particularly suitable are He/Cd, argon, nitrogen, metal vapour and NdYAG laser beams of multiplied frequency. It is known to the person skilled in the art that, for each selected light source, the suitable photoinitiator must be selected and, if necessary, sensitized. It has been found that the penetration depth of the radiation into the composition to be polymerized and the speed of working are in direct correlation with the absorption coefficient and the concentration of the photoinitiator. In stereolithography, preference is given to photoinitiators which enable the greatest radiation penetration depth into the compositions to be polymerized.

The invention thus also relates to a process for the polymerization of the novel compositions by irradiation thereof with actinic light. The polymers obtained can be used, for example, as coating compositions, photoresists, solder masks or adhesives.

If the compositions suitable according to the invention are employed as coating compositions, clear and hard coatings are obtained, for example on wood, paper, metal, ceramic or other surfaces. The coating thickness can be varied widely and can be, for example, from 1 μm to about 1 mm. The novel compositions can be used for the direct production of relief images for printed circuits or printing plates by irradiation of the mixtures, for example by means of a computer-controlled laser beam of suitable wavelength or using a photomask and an appropriate light source.

Another possible use of the novel compositions is as photocurable adhesives.

The novel compositions are preferably used for the production of photopolymerized layers, in particular in the form of three-dimensional objects built up from a plurality of mutually adherent, solidified layers.

Accordingly, the invention furthermore relates to a process for the production of three-dimensional objects from a composition suitable according to the invention by means of a lithographic process, in particular a stereolithographic process, where the surface of a layer of the novel composition is irradiated over the entire area or in a predetermined pattern with a UV and/or VIS light source so that a layer solidifies in the desired layer thickness in the irradiated areas, a new layer of the composition is then formed on the solidified layer and is likewise irradiated over the entire area or in a predetermined pattern, and where three-dimensional objects comprising a plurality of mutually adherent, solidified layers are obtained by repeated coating and irradiation.

The light source used in this process is preferably a laser beam, which, in a particularly preferred embodiment, is computer-controlled.

The examples below illustrate the present invention in greater detail, but are not intended to represent a limitation.

EXAMPLE 1

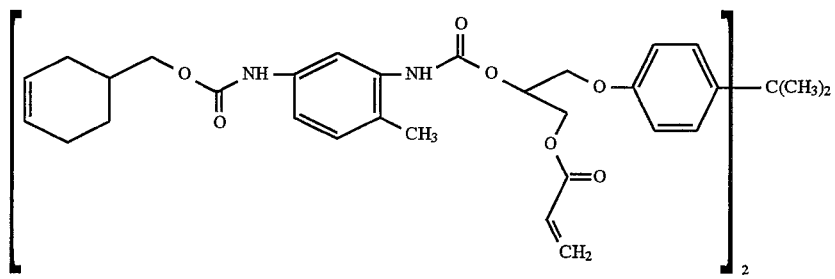

71.88 g (0.41 mol) of tolylene diisocyanate, 0.52 g of dibutyltin dilaurate and 0.2 g of Ralox® 46 are warmed to 35° C. in a reaction vessel while a stream of air is passed in. 100 g (0.206 mol) of bisphenol A diglycidyl diacrylate (Novacure 3700, UCB), dissolved in 200 ml of toluene, are slowly added dropwise, during which slight exothermicity is observed. The resultant mixture is stirred at 35° C. for about 5 hours until the isocyanate content has dropped to 1.12 eq/kg. 46.2 g (0.412 mol) of tetrahydrobenzyl alcohol are then slowly added dropwise. The reaction is slightly exothermic. The mixture is stirred at 35° C. until the isocyanate content is <0.02 eq/kg (about 11 hours). The removal of the solvent by distillation in a high vacuum (HV) gives a viscous, yellow resin of the above structure.

GPC (gel permeation chromatography): Mn=1390, Mw=2090

EXAMPLE 2

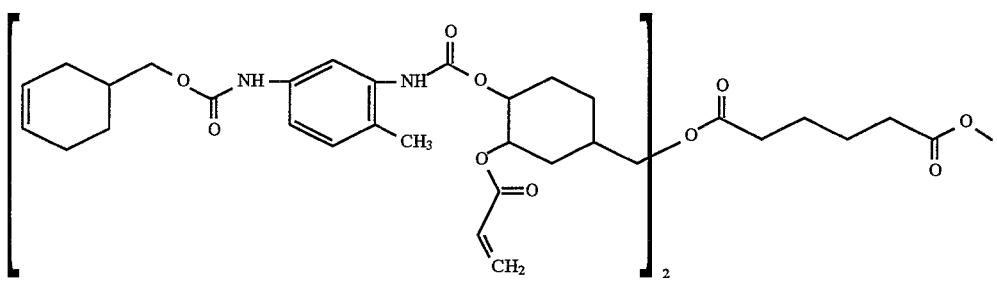

136.44 g (0.78 mol) of tolylene diisocyanate, 1.48 g of dibutyltin dilaurate and 1.02 g of Ralox® 46 are warmed to 35° C. in a reaction vessel while a stream of air is passed in. 200 g (0.38 mol) of the product of the reaction of acrylic acid and the cycloaliphatic epoxy resin

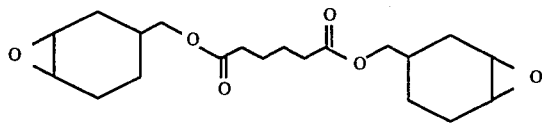

(Araldit CY 177, Ciba-Geigy), dissolved in 400 ml of chloroform, are slowly added dropwise. The exothermic reaction is held at 35° C. by means of an ice bath. After about 2.5 hours, an isocyanate content of 0.75 eq/kg has been reached. 87.48 g (0.78 mol) of tetrahydrobenzyl alcohol are then added dropwise, and the mixture is stirred until the isocyanate content has dropped to <0.08 eq/kg (about 2 hours). The solvent is removed by distillation in an HV. The product obtained has the above structure.

a reaction vessel. 100 g (0.206 mol) of Novacure 3700, dissolved in 100 ml of toluene, are slowly added dropwise at such a rate that the temperature can be kept at 35° C. The mixture is stirred until an isocyanate content of 1.6 eq/kg is obtained (about 5 hours). 61.90 g (0.412 mol) of TCD alcohol E [8(9)-hydroxytricyclo[$5.2.1.0^{2,6}$]dec-3-ene, Hoechst] are then added dropwise, and the mixture is stirred at 35° C. until the isocyanate content has dropped to <0.1 eq/kg (about 12 hours). The solvent is removed in an HV. The resultant product conforms to the above structure.

GPC: Mn=1430, Mw=265

EXAMPLE 3

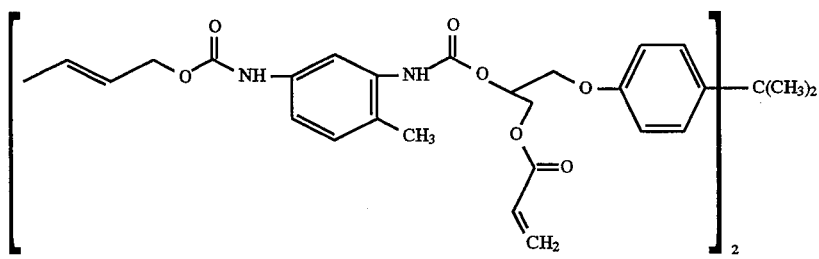

81.9 g (0.41 mol) of tolylene diisocyanate, 0.52 g of dibutyltin dilaurate and 0.52 g of Ralox® 46 are heated to 35° C. in a reaction vessel. 100 g (0.206 mol) of bisphenol A diglycidyl diacrylate (Novacure 3700), dissolved in 100 ml of toluene, are slowly added dropwise. The mixture is held at 35° C. by means of an ice bath. After about 2 hours, an isocyanate content of 1.7 eq/kg has been reached. 29.71 g (0.41 mol) of crotyl alcohol are then added dropwise. The solution is stirred at 35° C. until the isocyanate content has dropped to <0.08 eq/kg. The solvent is removed by distillation in an HV. The product obtained has the above structure.

EXAMPLE 4

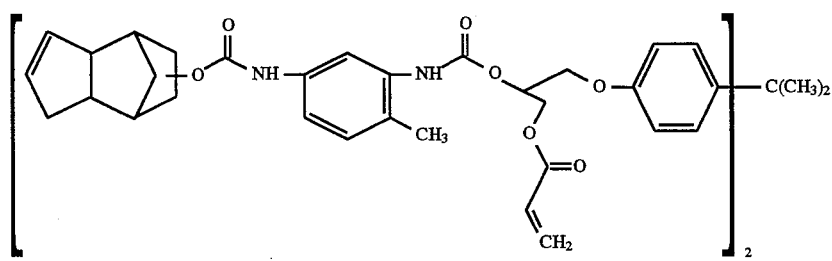

71.9 g (0.206 mol) of tolylene diisocyanate, 0.52 g dibutyltin dilaurate and 0.52 g of Ralox® 46 are warmed to 35° C. in

EXAMPLE 5

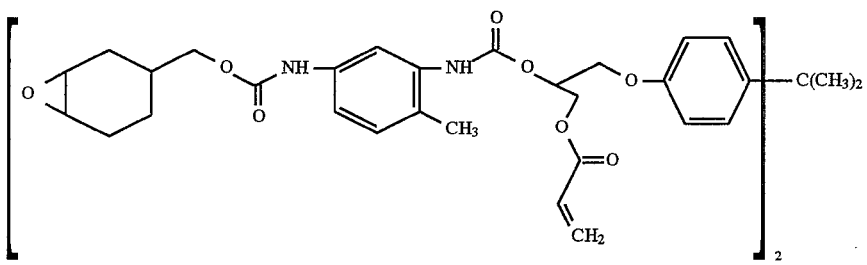

138.4 g (0.13 mol) of the product from Example 1, 10 g of sodium acetate and 0.65 g of hydroquinone monomethyl ether are suspended in 200 ml of chloroform. 68.8 g (0.37 mol) of 40% peracetic acid are slowly added dropwise, during which the temperature must not rise above 40° C. The reaction mixture is stirred at 35° C. for a further 4 hours and then extracted with 5% aqueous NaHCO$_3$ and twice with water. After the organic phase has been dried using MgSO$_4$ and the peroxides remaining have been destroyed using NaHSO$_3$, the solvent is removed by distillation in an HV. The product has the above structure.

GPC: Mn=1370, Mw=2590

Epoxide content: 1.84 eq/kg (60% of theory).

71.9 g (0.412 mol) of tolylene diisocyanate, 0.52 g of dibutyltin dilaurate and 0.52 g of Ralox® 46 are warmed to 35° C. with stirring in a reaction vessel. 100 g (0.206 mol) of Novacure 3700, dissolved in 100 ml of toluene, are slowly added dropwise. The mixture is stirred at 35° C. for about 2 hours until an isocyanate content of 1.6 eq/kg has been reached. 36.3 g (0.42 mol) of hydroxyethyl vinyl ether are then added dropwise. After a further 6 hours at 35° C., an isocyanate content of <0.02 eq/kg has been reached. The solvent is removed by distillation in an HV. The resultant product has the above structure.

GPC: Mn=1970, Mw=5300 Double-bond content: 3.1 eq/kg (78% of theory).

EXAMPLE 6

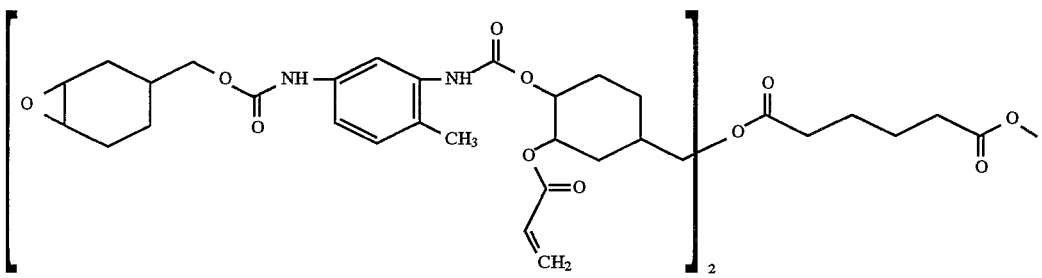

209 g (0.19 mol) of the reaction product from Example 2, 15 g of sodium acetate and 1 g of hydroquinone monomethyl ether are suspended in about 500 ml of chloroform. 101.1 g (0.53 mol) of 40% peracetic acid are slowly added dropwise, during which the temperature must not rise above 35° C. The mixture is then stirred at 35° C. for a further 4 hours. The mixture is extracted with 5% NaHCO$_3$ and twice with water, and the organic phase is dried and, after removal of the peroxides remaining, is evaporated in an HV.

GPC: Mn 1020, Mw=2240 Epoxide content: 1.12 eq/kg (61.8% of theory); chemical formula: see above.

EXAMPLE 7

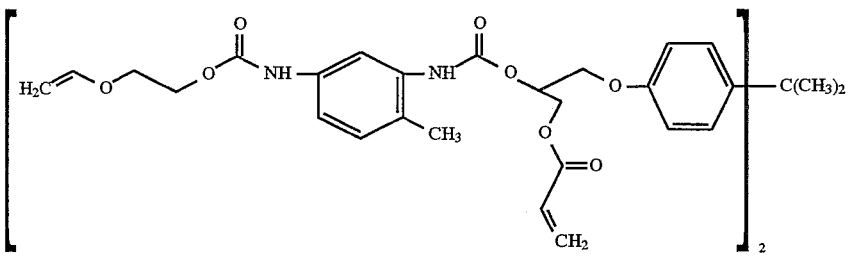

EXAMPLE 8

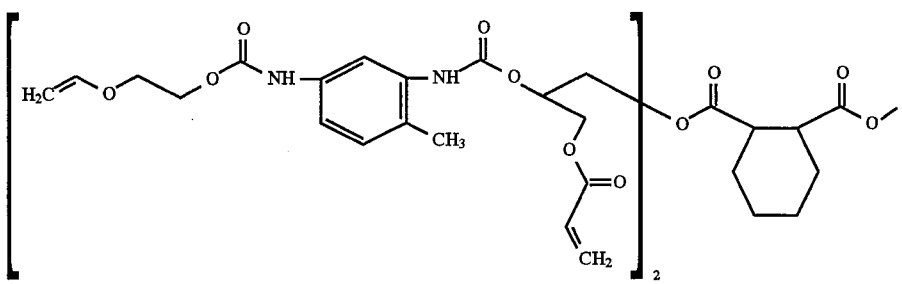

71.75 g (0.412 mol) of tolylene diisocyanate, 0.52 g of dibutyltin dilaurate and 0.48 g of Ralox® 46 are warmed to 35° C. with stirring in a reaction vessel. 88.25 g (0.206 mol) of the product of the reaction of diglycidyl hexahydrophthalate and acrylic acid, dissolved in 100 ml of toluene, are slowly added dropwise. The mixture is stirred at 35° C. until an isocyanate content of 1.0 eq/kg has been reached. 36.3 g (0.412 mol) of hydroxyethyl vinyl ether are then added dropwise. After a further 2 hours at 35° C., an isocyanate content of <0.02 eq/kg has been reached. The solvent is removed by distillation in an HV. The resultant product has the above structure.

GPC: Mn=1900, Mw=6600

EXAMPLE 9

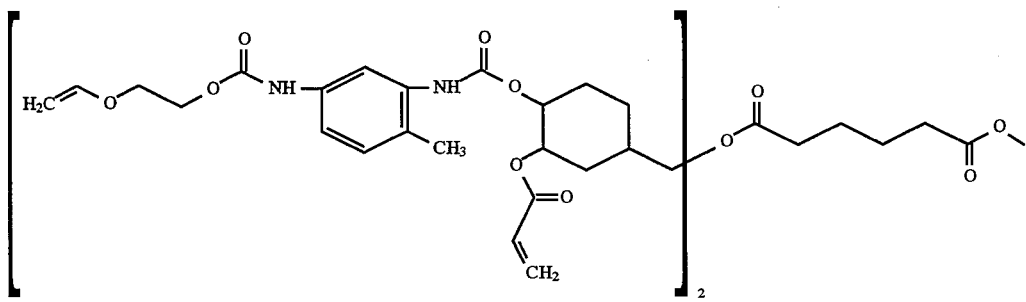

71.75 g (0.412 mol) of tolylene diisocyanate, 0.52 g of dibutyltin dilaurate and 0.53 g of Ralox® 46 are warmed to 35° C. with stirring. 105.18 g (0.206 mol) of the product of the reaction of

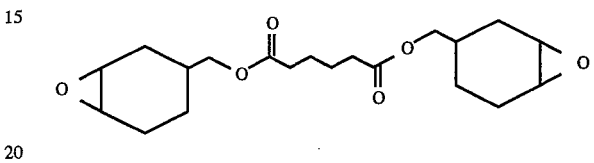

and acrylic aid, dissolved in 100 ml of toluene, are added dropwise. After about 5 hours at 35° C., an isocyanate content of 1.1 eq/kg has been reached. 36.3 g (0.412 mol) of hydroxyethyl vinyl ether are then added dropwise. After about 2 hours at 35° C., an isocyanate content of <0.05 eq/kg has been reached. The solvent is removed by distillation in an HV. The resultant product has the above structure.

GPC: Mn=1100, Mw=2100

EXAMPLE 10

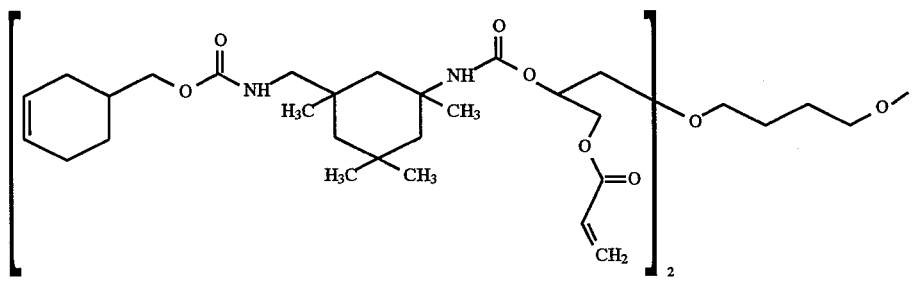

100 g (0.29 mol) of isophorone diisocyanate and 0.58 g of benzoyl chloride are heated to 35° C. with stirring. 65.06 g (0.58 mol) of tetrahydrobenzyl alcohol are added dropwise, and the mixture is stirred at 35° C. until an isocyanate content of 3.13 eq/kg is obtained (about 8 hours). 100 g (0.29 mol) of Laromer 8765 (butanediol diglycidyl ether diacrylate), dissolved in 100 ml of toluene, are then added dropwise. The mixture is stirred at 35° C. for 34 hours until an isocyanate content of 0.09 eq/kg is obtained. The solvent is removed by distillation in an HV, giving a very high-viscosity resin of the above structure.

GPC: Mn=1000, Mw=1840 monomethyl ether are added. 53.24 g (0.28 mol) of 40% peracetic acid are then slowly added dropwise. The solution is stirred at 35° C. for a further 6 hours and worked up as in Example 5. The resultant product has the above structure.

Yield: 83.9 g (81.8%) Epoxide content: 1.25 eq/kg (65.2% of theory). GPC: Mn=1040, Mw=1940

EXAMPLE 11

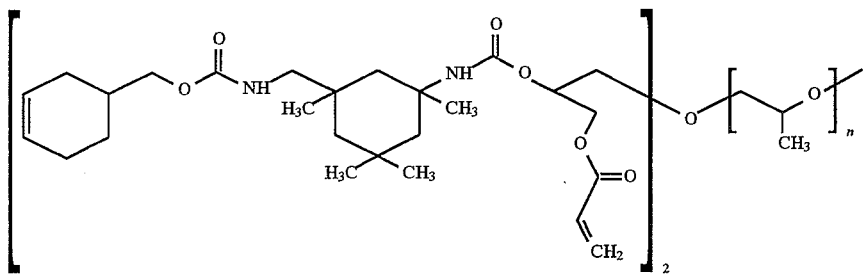

n = about 15

44.46 g (0.2 mol) of isophorone diisocyanate are heated to 35° C. together with 0.2 g of benzoyl chloride, and 22.43 g (0.2 mol) of tetrahydrobenzyl alcohol are added dropwise with stirring. The mixture is stirred at 35° C. until an isocyanate content of 3.05 eq/kg is obtained (about 13 hours). 100 g (0.1 mol) of polypropylene glycol 400 diglycidyl ether diacrylate, dissolved in 100 ml of toluene, are then added dropwise. The solution is stirred until an isocyanate content of 0.13 eq/kg is obtained (about 38 hours). The solvent is removed in an HV. The resultant product has the above structure.

GPC: Mn=1280, Mw=2360

EXAMPLE 12

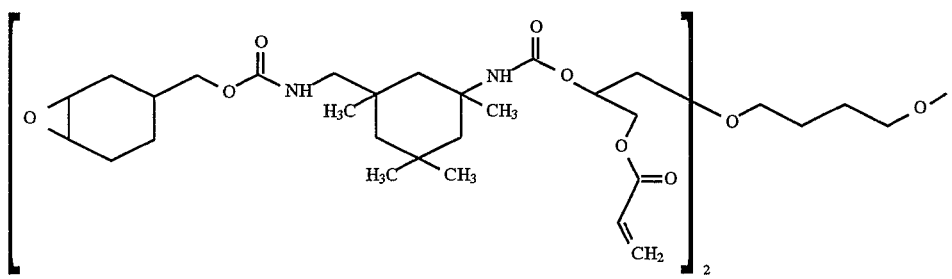

100 g (0.098 mol) of the product from Example 10 are dissolved in 200 ml of chloroform, and the solution is heated to 35° C. 10 g of sodium acetate and 0.49 g of hydroquinone

EXAMPLE 13

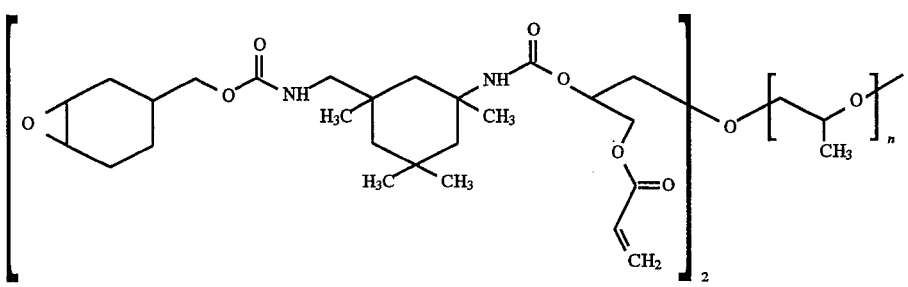

100 g (0.06 mol) of the product from Example 11 are dissolved in 200 ml of chloroform, and the solution is heated to 35° C. 10 g of sodium acetate and 0.43 g of hydroquinone monomethyl ether are added. 31.9 g (0.168 mol) of 40% peracetic acid are then slowly added dropwise. The solution is stirred at 35° C. for a further 5 hours and worked up as in Example 5. The resultant product has the above structure.

Yield: 84.4 g (82.8%) Epoxide content: 1.05 eq/kg (89% of theory) GPC: Mn=930, Mw=1980

EXAMPLE 14

The following components are mixed at 60° C. in a round-bottom flask to give a homogeneous composition:

50% of the product from Example 6

20% of CY 179 (cycloaliphatic epoxy resin, Ciba-Geigy)

20% of Sartomer 454 (ethoxylated trimethylolpropane triacrylate)

8.4% of Sartomer 213 (butanediol diacrylate)

0.6% of Cyracure UVI 6974

1% of Irgacure 184

The composition has a viscosity of 443 cps at 30° C. With the aid of an He-Cd laser, a moulding with a curl factor of 0.5% is produced using the "weave" structure.

In stereolithography, a process-specific measure of shrinkage-induced deformation is the "curl factor" (for measurement of the cud factor, cf. Proceedings 2nd Int. Conference in Rapid Prototyping, Dayton, Ohio, (1991), or P. F. Jacobs, Rapid Prototyping and Manufacturing, Soc. Manufact. Eng., 1992, p. 40 ff.). The curl factor is determined on test specimens produced by stereolithography, involving measurement of the deformation of a self-supporting part of the test specimen caused by shrinkage. The curl factor is the difference between the heights of a fixed part of a test specimen and an unfixed, deformed part, divided by the length of the self-supporting piece, in %.

EXAMPLE 15

The following components are mixed at 60° C. in a round-bottom flask until a homogeneous composition has been prepared:

33.5% of the product from Example 5

15% of SR 344 (polyethylene glycol 400 diacrylate)

3% of Pleximon V773 (neopentyl glycol dimethacrylate)

2% of SR 306 (tripropylene glycol diacrylate)

40% of SR 348 (ethoxylated bisphenol A dimethacrylate)

0.15% of hydroquinone monomethyl ether 5.85% of Irgacure 184

0.5% of Cyracure UVI 6974

The composition has a viscosity of 1720 cps at 30° C. With the aid of an He-Cd laser, mouldings are produced which, after laser curing, have a modulus of elasticity of 52N/mm². After complete curing (30 minutes UV, 30 minutes 130° C.), a modulus of elasticity of 1640N/mm² and an elongation at break of 2% are obtained. The curl factor (weave structure) is 15%.

EXAMPLE 16

The following components are mixed at 60° C. in a round-bottom flask until a homogeneous composition has been achieved:

43% of CY 179

30% of the product from Example 7

25% of Rapicure DVE 3 (triethylene glycol divinyl ether, GAF)

1% of Irgacure 184

1% of Cyracure UVI 6974

The composition has a viscosity of 274 cps at 30° C. Mouldings are produced with the aid of an He-Cd laser. After laser curing, the modulus of elasticity is 3.1N/mm², and after complete curing (30 minutes UV, 30 minutes 130° C.), a modulus of elasticity of 2240N/mm² and an elongation, at break of 2.4% are measured.

EXAMPLE 17

The following components are mixed at 60° C. in a round-bottom flask until a homogeneous composition has been achieved:

46% of CY 179

10% of DY 026 (butanediol diglycidyl ether)

30% of the product from Example 7

12% of SR 399 (dipentaerythritol monohydroxypentaacrylate)

1% of Irgacure 184

1% of Cyracure UVI 6974

The composition has a viscosity of 2610 cps at 30° C. Mouldings are produced with the aid of an He-Cd laser. After laser curing, the modulus of elasticity is 8.8N/mm². After complete curing, (30 minutes UV, 30 minutes 130° C.), a modulus of elasticity of 3021N/mm² and an elongation at break of 11% are measured.

EXAMPLE 18

The following components are mixed at 60° C. in a round-bottom flask until a homogeneous composition has been achieved:

33.5% of the product from Example 8

15% of SR 344

3% of Pleximon V 773

2% of SR 306

40% of SR 348

0.15% of hydroquinone monomethyl ether 5.85% of Irgacure 184

0.5% of Cyracure UVI 6974

The composition has a viscosity of 1610 cps at 30° C. Mouldings are produced with the aid of an He-Cd laser. After laser curing, the modulus of elasticity is 50N/mm². After complete curing, a modulus of elasticity of 2409N/mm² and an elongation at break of 4.2% are obtained. The curl factor (weave structure) is 15%.

EXAMPLE 19

The following components are mixed at 60° C. in a round-bottom flask until a homogeneous composition has been achieved:

33.5% of the product from Example 9

15% of SR 344

3% of Pleximon V 773

2% of SR 306

40% of SR 348

0.15% of hydroquinone monomethyl ether 5.85% of Irgacure 184

0.5% of Cyracure UVI 6974.

The composition has a viscosity of 4310 cps at 30° C. Mouldings are produced with the aid of an He-Cd laser. After laser curing, the modulus of elasticity is 40N/mm². After complete curing, a modulus of elasticity of 2126N/mm² and an elongation at break of 2% are obtained. The curl factor (weave structure) is 14%.

EXAMPLE 20

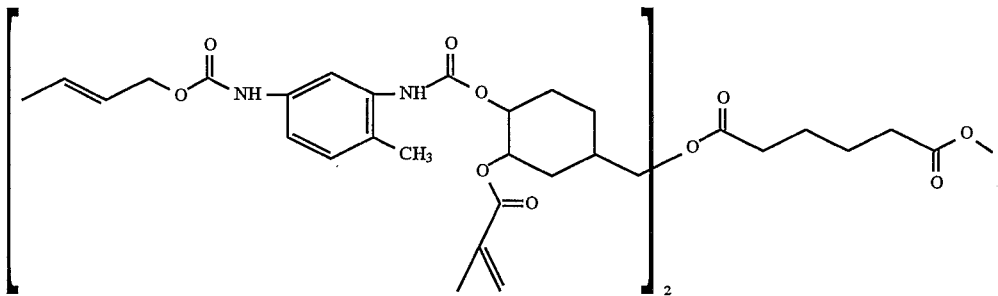

64.92 g (0.372 mol) of tolylene diisocyanate, 0.47 g of dibutyltin dilaurate, 0.5 g of Ralox® 6 and 100 ml of toluene are warmed to 35° C. with stirring in a reaction vessel. 100 g (0.186 mol) of the product of the reaction of Araldit CY 177 and methacrylic acid (see Example 2) are slowly added dropwise. The exothermic reaction is held at 35° C. by means of an ice bath. After about 10 hours, an isocyanate content of 1.54 eq/kg is obtained. 26.83 g (0.372 mol) of crotyl alcohol are then added dropwise, and the mixture is stirred until an isocyanate content of 0.06 eq/kg has been achieved (about 64 hours). The solvent is removed by distillation in a high vacuum. The resultant product has the above structure.

GPC: Mn=1390, Mw=2990

EXAMPLE 21

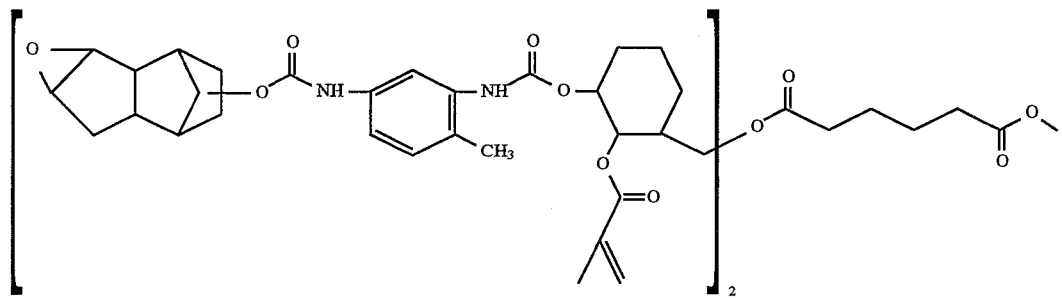

64.8 g (0.372 mol) of tolylene diisocyanate, 0.47 g of dibutyltin dilaurate, 0.5 g of Ralox® 46 and 100 ml of toluene are warmed to 35° C. with stirring in a reaction vessel. 100 g (0.186 mol) of the product of the reaction of Araldit CY 177 and methacrylic acid (see Example 2), diluted with 50 ml of toluene, are slowly added dropwise, during which the temperature is held at 35° C. After about 3 hours, an isocyanate content of 1.47 eq/kg is obtained. 61.83 g (0.372 mol) of epoxidized TCD alcohol (prepared by oxidation of TCD alcohol E by means of 40% peracetic acid) are then added dropwise, and the mixture is stirred until an isocyanate content of 0.019 eq/kg is obtained (about 26 hours). The solvent is removed by distillation in a high vacuum. The resultant product has the above structure.

GPC: Mn=1150, Mw=2530

What is claimed is:

1. A composition comprising a) from 5 to 99% by weight of a monomeric, polymerizable (meth)acrylate of the formula I containing urethane groups,

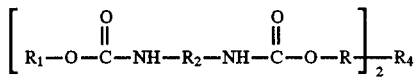 (I)

in which
R is a divalent group of the formula

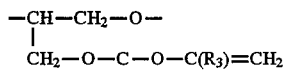

or

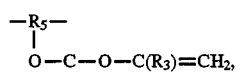

$R_1$ is a cationically polymerizable group or a free-radical-polymerizable group, with the exception of the acrylate and allyl groups, $R_2$ is an aliphatic, cycloaliphatic or aromatic radical, $R_3$ is hydrogen or $CH_3$, $R_4$ is the radical of an aliphatic, cycloaliphatic or aromatic diglycidyl compound after removal of the diglycidyl radical, or is the radical of a cycloaliphatic diepoxide, and $R_5$ is a cycloaliphatic bridge, b) from 1 to 10% by weight of a free-radical photoinitiator, c) from 0 to 20% by weight of conventional additives, d) from 0 to 80% by weight of one or more mono-, di- or polyfunctional (meth)acrylates or mixtures thereof, e) from 0 to 80% by weight of a di- or polyfunctional epoxide, or mixtures thereof, f) from 0 to 50% by weight of an OH-terminated polyether or polyester, or mixtures thereof, g) from 0 to 5% by weight of a cationic photoinitiator, and h) from 0 to 80% by weight of one or more mono-, di- or polyfunctional vinyl ethers, where the proportion of components a) to h) together is 100% by weight.

2. A composition according to claim 1, in which $R_1$ is a cationically polymerizable group of the formula

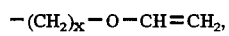

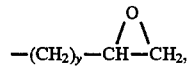

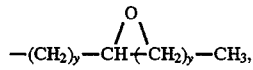

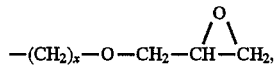

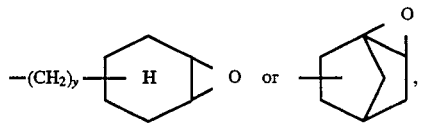

or a free-radical-polymerizable group of the formula

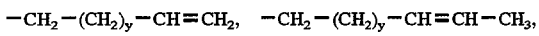

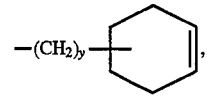

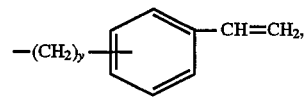

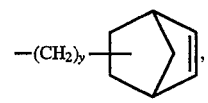

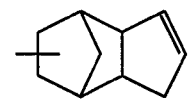

or

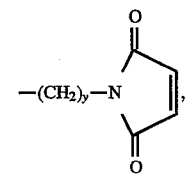

in which x is an integer from 2 to 20, and y is an integer from 1 to 20.

3. A composition according to claim 2, in which $R_1$ is a cationically polymerizable group.

4. A composition according to claim 1, in which $R_2$ end $R_4$, independently of one another, are a $C_4$–$C_{20}$ aliphatic bridge, which may be interrupted by at least one ether, ester, urethane, amide or arylene group, and furthermore are a cycloaliphatic or aromatic bridge.

5. A composition according to claim 4, in which $R_2$ is a $C_4$–$C_{20}$ aliphatic or an aromatic bridge or a plurality of aromatic groups interrupted by aliphatic groups.

6. A composition according to claim 4, in which $R_4$ is a $C_4$–$C_{20}$ aliphatic bridge interrupted by at least one ether or ester group, or is an aromatic bridge.

7. A composition according to claim 2, in which x and y are integers from 1 to 6.

8. A method for the production of coating compositions, adhesives, photoresists and solder masks which comprises mixing components a) and b) of a composition according to claim 1 in a vessel, optionally, in the absence of light and at an elevated temperature.

9. A process for the polymerization of a composition according to claim 1 comprising irradiating the composition with actinic light.

10. A process for the production of three-dimensional objects from a composition according to claim 1 by a lithographic process, where the surface of a layer of this composition is irradiated over the entire area or in a predetermined pattern with a UV and/or VIS light source so that a layer solidifies in the desired layer thickness in the irradiated areas, a new layer of this composition is then formed on the solidified layer and is likewise irradiated over the entire area or in a predetermined pattern, and where three-dimensional objects comprising a plurality of mutually adherent, solidified layers are obtained by repeated coating and irradiation.

11. A process according to claim 10, in which the light source used is a laser beam.

12. A method according to claim 8 wherein the composition is mixed in a vessel in the absence of light.

13. A method according to claim 12 wherein the composition is mixed in a vessel at an elevated temperature of from about 50° to 70° C.

14. A process according to claim 11, in which the light source is a computer-controlled laser beam.

* * * * *